(12) United States Patent
Sklar et al.

(10) Patent No.: US 7,730,563 B1
(45) Date of Patent: Jun. 8, 2010

(54) HEAD SUPPORT AND STABILIZATION SYSTEM

(75) Inventors: Frederick Sklar, P.O. Box 2897, Waxahachie, TX (US) 75168; Charles E. Dinkler, II, Cincinnati, OH (US); Kevin R. Easton, Cincinnati, OH (US)

(73) Assignees: Frederick Sklar, Waxahachie, TX (US); Integra LifeSciences Corporation, Plainsboro, NJ (US)

( * ) Notice: Subject to any disclaimer, the term of this patent is extended or adjusted under 35 U.S.C. 154(b) by 1279 days.

(21) Appl. No.: 11/091,723

(22) Filed: Mar. 28, 2005

Related U.S. Application Data (60) Provisional application No. 60/557,212, filed on Mar. 29, 2004, provisional application No. 60/567,389, filed on Apr. 30, 2004.

(51) Int. Cl.
*A61G 13/12* (2006.01)
*A61B 19/00* (2006.01)

(52) U.S. Cl. .................... 5/637; 5/640; 5/622; 602/32; 602/33; 606/130

(58) Field of Classification Search .................... 5/637, 5/636, 632, 638, 640, 643, 622, 621, 725; 606/130; 602/32–37
See application file for complete search history.

(56) References Cited

U.S. PATENT DOCUMENTS

| | | | | |
|---|---|---|---|---|
| 2,494,792 A | * | 1/1950 | Bloom | 602/37 |
| 2,966,383 A | * | 12/1960 | Boetcker et al. | 5/637 |
| 3,072,118 A | * | 1/1963 | Standerwick et al. | 602/17 |
| 3,099,441 A | * | 7/1963 | Ries | 5/637 |
| 3,604,412 A | * | 9/1971 | Gardner | 602/37 |
| 3,835,861 A | * | 9/1974 | Kees et al. | 5/637 |
| 3,923,046 A | * | 12/1975 | Heifetz | 606/96 |
| 4,108,426 A | | 8/1978 | Lindstroem et al. | 5/637 |
| 4,169,478 A | * | 10/1979 | Hickmann | 606/151 |
| 4,360,028 A | | 11/1982 | Barbier et al. | 600/436 |
| 4,444,179 A | * | 4/1984 | Trippi | 602/37 |
| 4,457,300 A | | 7/1984 | Budde | 600/228 |
| 4,465,069 A | * | 8/1984 | Barbier et al. | 606/130 |
| 4,545,572 A | | 10/1985 | Day | 5/637 |
| 4,667,660 A | * | 5/1987 | Eingorn | 602/37 |
| 5,147,287 A | | 9/1992 | Jewell et al. | 602/32 |
| 5,197,965 A | * | 3/1993 | Cherry et al. | 606/54 |
| 5,214,815 A | | 6/1993 | Agbodoe et al. | 5/637 |
| 5,254,079 A | * | 10/1993 | Agbodoe et al. | 602/32 |
| 5,269,034 A | * | 12/1993 | Day et al. | 5/637 |
| 5,276,927 A | * | 1/1994 | Day | 5/622 |
| 5,284,129 A | | 2/1994 | Agbodoe et al. | 600/230 |
| 5,317,771 A | | 6/1994 | Cook | 5/637 |
| 5,318,509 A | * | 6/1994 | Agbodoe | 602/32 |
| 5,347,894 A | * | 9/1994 | Fischer | 81/471 |

(Continued)

*Primary Examiner*—Robert G Santos
(74) *Attorney, Agent, or Firm*—Scott T. Griggs; Griggs Bergen LLP (57) ABSTRACT

A head support system that has a fixation arc system that is adjustable both vertically and horizontally and is mounted to a patient support structure. The fixation arc system is positionable adjacent to, and provides lateral support for, the patient's head. A pin support is connected to, and extends from the fixation arc system. A pin is adjustably mounted to the pin support and contacts the patient's head to provide a lateral fixation thereof. The pin has a centerline that is rotatable about two axes of motion substantially perpendicular to the pin centerline.

7 Claims, 10 Drawing Sheets

U.S. PATENT DOCUMENTS

| | | | |
|---|---|---|---|
| 5,529,358 A | 6/1996 | Dinkler et al. | 600/233 |
| 5,537,704 A * | 7/1996 | Dinkler | 5/622 |
| 5,564,663 A | 10/1996 | Cook et al. | 248/222.12 |
| 5,674,186 A * | 10/1997 | Guigui et al. | 602/17 |
| 6,117,143 A | 9/2000 | Hynes et al. | 606/130 |
| 6,179,846 B1 | 1/2001 | McFadden et al. | 606/130 |
| 6,306,146 B1 * | 10/2001 | Dinkler | 606/130 |
| 6,315,783 B1 | 11/2001 | Katz et al. | 606/130 |
| 6,368,330 B1 * | 4/2002 | Hynes et al. | 606/130 |
| 6,381,783 B2 * | 5/2002 | Reinhardt et al. | 5/622 |
| 6,584,630 B1 * | 7/2003 | Dinkler | 5/622 |
| 6,629,982 B2 * | 10/2003 | Day et al. | 606/130 |
| 6,684,428 B2 | 2/2004 | Grotenhuis et al. | 5/637 |
| 6,770,082 B2 | 8/2004 | Dominguez et al. | 606/130 |
| 7,229,451 B2 * | 6/2007 | Day et al. | 606/130 |
| 7,507,244 B2 * | 3/2009 | Dinkler | 606/130 |
| 2001/0029379 A1 * | 10/2001 | Grotehuis et al. | 606/130 |
| 2002/0042619 A1 * | 4/2002 | Dominguez et al. | 606/130 |
| 2002/0151907 A1 * | 10/2002 | Day et al. | 606/130 |
| 2004/0097985 A1 * | 5/2004 | Day et al. | 606/151 |
| 2005/0075650 A1 * | 4/2005 | Dinkler | 606/130 |

* cited by examiner

HEAD SUPPORT AND STABILIZATION SYSTEM

This application claims the benefit of U.S. Provisional Application No. 60/557,212, filed on Mar. 29, 2004 and U.S. Provisional Application No. 60/567,389, filed on Apr. 30, 2004, all of which are hereby expressly incorporated by reference herein

FIELD OF THE INVENTION

This invention relates to surgical equipment and more particularly, to a head support system.

BACKGROUND OF THE INVENTION

During surgical procedures, one or more devices may be used to support a patient's head. For example, there may be a need to provide a static support for a patient's head; and typically, a static head support includes one or more pads that provide a static subjacent support of the patient's head in a prone or supine position. Such a static head support is mounted on a crossbar that extends transversely off the end of a patient support such as an operating table. Alternatively, a stabilization device, such as a skull clamp, is also used to support and stabilize a patient's head, and such a skull clamp is also mounted on the crossbar. In some applications, both static head support and skull clamp stabilization are desired, and then both devices must be mounted on the crossbar. In those situations where both subjacent support and lateral stabilization are required, having to mount both devices from the same crossbar member is complicated, inflexible and inconvenient. Therefore, there is a need to provide a support structure for a head support and a stabilization device that is more convenient and flexible to use.

Children around two years old and younger also present special issues with respect to a head support system. Such young children do not often have a bone structure that permits the use of known skull clamps, and therefore, other head support systems are required. While it is known to use a horseshoe pad to support a child's head, a horseshoe pad does provide any lateral support or stabilization of the child's head. Therefore, there is a need for a head support system for a child that provides both subjacent and lateral support of the child's head.

Therefore, there is a need to provide structure for more flexibly mounting head support and stabilization devices.

SUMMARY OF THE INVENTION

The present invention provides a head support and fixation system that is highly flexible and can be used with a wide range of neuro-navigational and surgical procedures. The head support and fixation system of the present invention provides separate and independent support and stabilization devices, thereby providing greater flexibility and convenience to the user. The head support and fixation system of the present invention can be located close to an end of a patient support table, which permits a more complete support for smaller patients and minimizes stress and strain on the patient's muscular and skeletal systems. The head support and fixation system of the present invention is compact and does not require use of a base unit for supporting a skull clamp and therefore, provides more convenient and open access to smaller patients.

According to the principles of the present invention and in accordance with the described embodiments, the invention provides a head support system that supports and stabilizes a patient's head. The head support system has a fixation arc system that is adjustably mounted to a patient support structure and is positionable adjacent to, and provides lateral support for, the patient's head. A pin support is connected to, and extends from the fixation arc system. A pin is adjustably mounted to the pin support and contacts the patient's head to provide a lateral fixation thereof. The pin has a centerline that is rotatable about two axes of motion substantially perpendicular to the pin centerline. In one aspect of this invention, the fixation arc is adjustable both vertically and horizontally.

In another embodiment, the invention provides a head support system for use with a patient support and provides support and stabilization for a patient's head. The head support system has a support structure connected to the patient support, and a horseshoe support system connected to the support structure for subjacent support of the patient's head. An auxiliary bracket is connected to the support structure and has a connector for receiving other devices used in a surgical procedure. In one aspect of this invention, the auxiliary bracket includes a generally horizontal arm and a generally vertical post.

These and other objects and advantages of the present invention will become more readily apparent during the following detailed description taken in conjunction with the drawings herein.

DETAILED DESCRIPTION OF THE INVENTION

Figure 1:
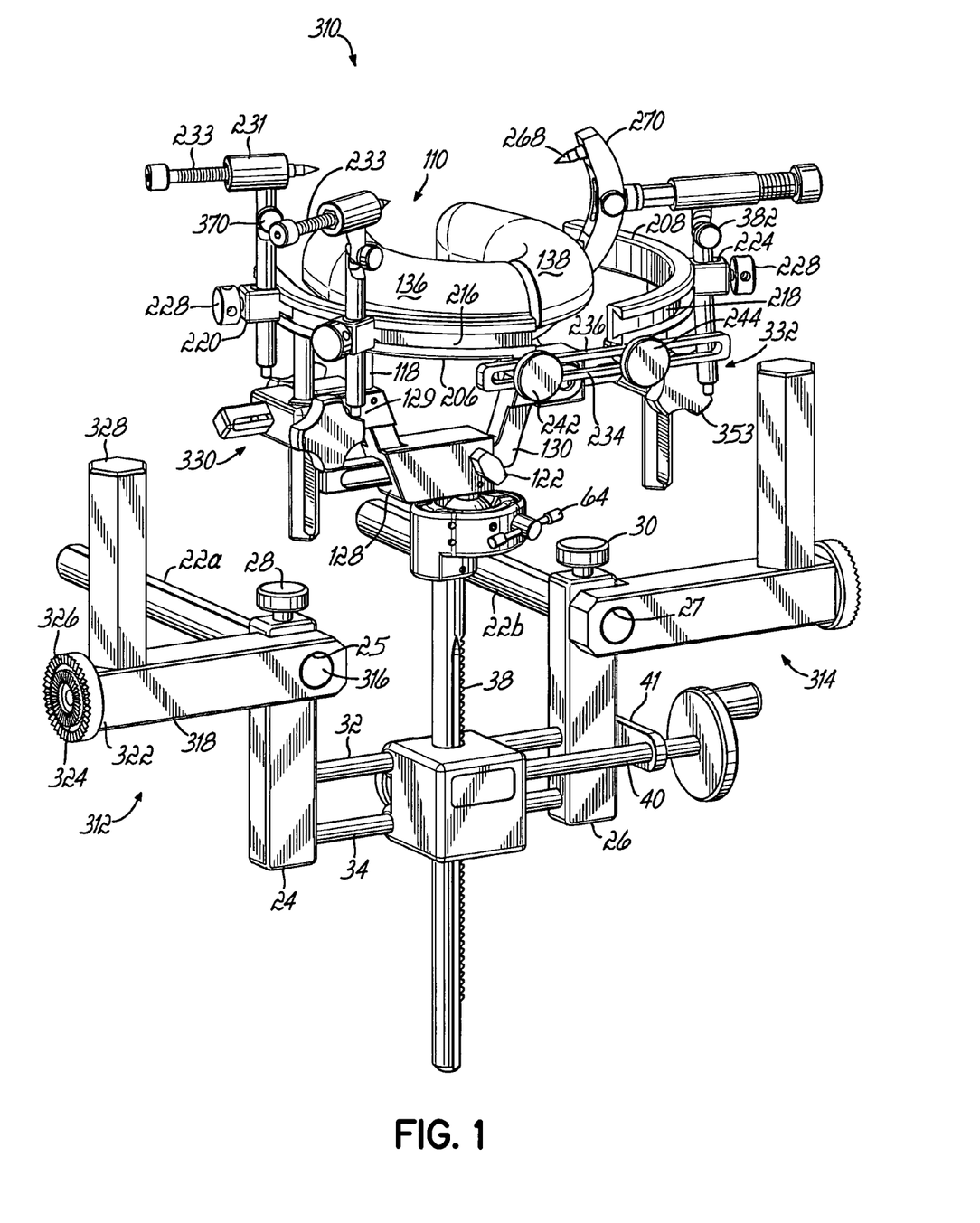
FIG. 1 is a first outer end perspective view of a head support and fixation system in accordance with the principles of the present invention.

Referring to FIG. 1, in a first embodiment, a head support and stabilization system 310 is mounted on spaced-apart support shafts 22a, 22b that are connected in a known manner to an end of a patient support (not shown), for example, an operating table. The support shafts 22a, 22b extend substantially parallel with a length of the patient support. First and second support posts 24, 26 have respective bores 25, 27 (FIG. 2) that receive respective support shafts 22a, 22b. The support posts 24, 26 can be locked at a desired position by means of respective locking screws 28, 30. Upper and lower guide rods 32, 34 (FIG. 1) have first ends fixed in a lower portion of the first support post 24. Opposite ends of the guide rods 32, 34 are supported in a first, lower portion of the second support post 26. The guide rods 32, 34 extend through a gear box housing 36, and thus, the housing 36 is slidable longitudinally along the guide rods 32, 34 but cannot rotate with respect thereto. Also extending through the housing 36 is a gear rack 38 which is used to raise and lower a head support device, for example, pads 136, 138 by rotating a crank rod 40. The crank rod 40 is supported by a bracket 41 rigidly connected to the support post 26.

Figure 3:
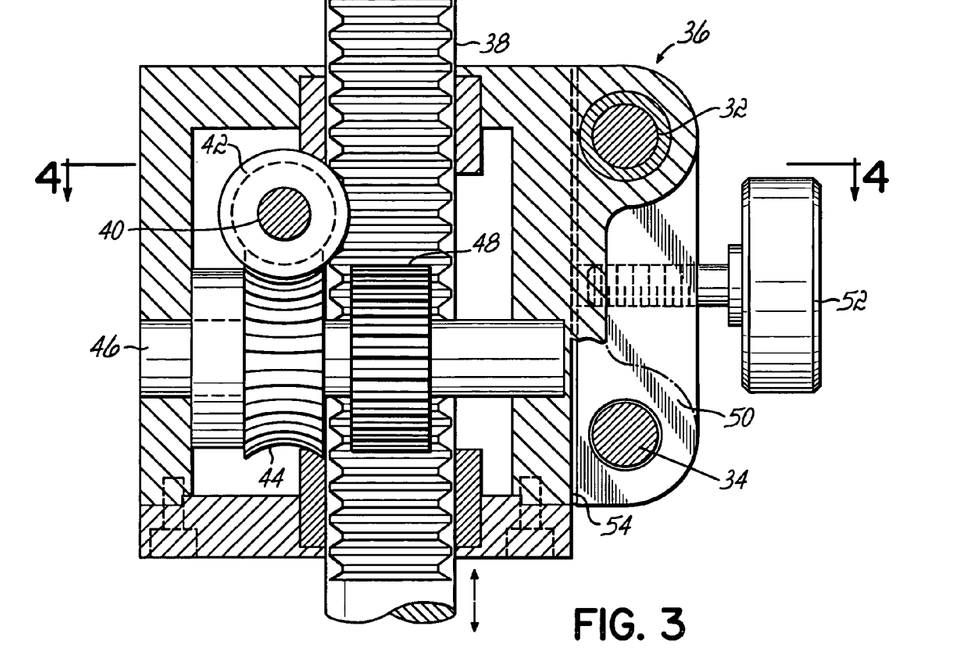
FIG. 3 is a cross-sectional view of interior components of a gear box used with the head support and fixation system of FIG. 1.
Figure 4:
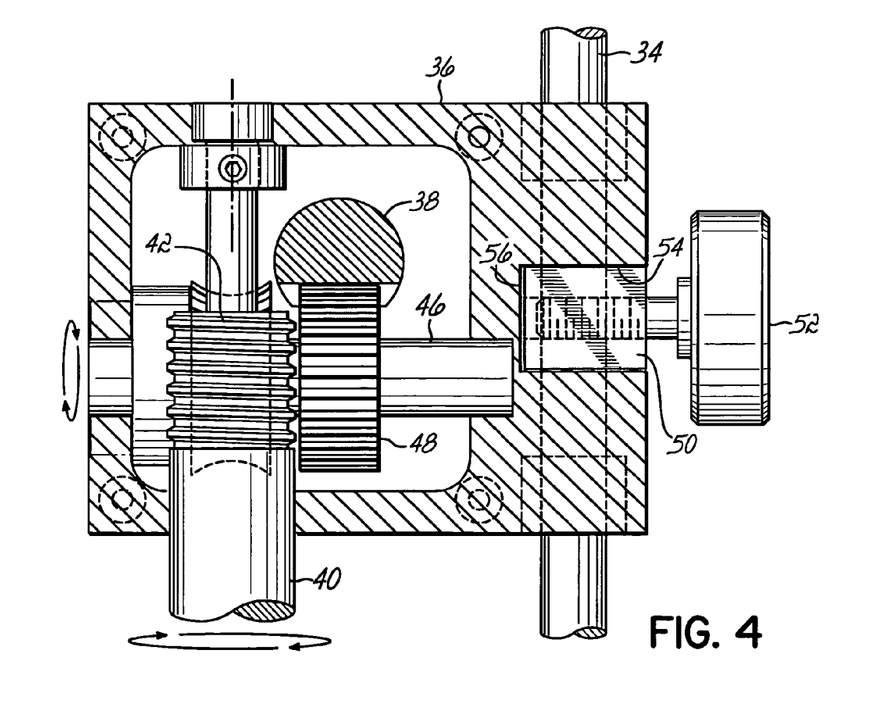
FIG. 4 is a cross-sectional view taken along line 4-4 of FIG. 3 and illustrates locking components of the gear box used with the head support and fixation system of FIG. 1.

Referring to FIG. 3, within the gear box 36, a worm 42 is mounted on an end of the crank rod 40. The worm 42 meshes with a worm gear 44 that is fixed on a shaft 46 that, in turn, also carries a spur gear 48. The spur gear 48 meshes with the gear rack 38. Thus, rotation of the crank rod 40 rotates the worm 42 that, in turn, rotates the worm gear 44 and spur gear 48, thereby moving the gear rack 38 either up or down depending on the direction of rotation of the crank shaft 40. The worm 42 and worm gear 44 hold the gear rack 38 in its desired position without the need for a further mechanical lock. The gear box 36 is securable on the guide rods 32, 34 by means of a locking bar 50 and lock screw 52 that is threaded into the locking bar 50. The locking bar 50 is also mounted on the guide rods 32, 34 and, as shown in FIG. 4, is mounted in a slot 54 of the gear box housing 36. With the lock screw 52 in the position illustrated in FIGS. 3 and 4, the gear box 36 is free to be moved over the length of the guide rods 32, 34. However, rotation of the lock screw 52 in a direction advancing the lock screw 52 through the locking bar 50, results in the lock screw 52 contacting the bottom surface 56 of the slot 54. Further, rotation of the lock screw 52 in the same direction pushes the locking bar 50 outward, that is, to the right, as illustrated in FIG. 4, thereby pressing the locking bar 50 tightly against the guide rods 32, 34 and securing the gear box 36 in a desired position with respect thereto.

In the embodiment of the head support and fixation system 310 shown in FIG. 1, a skull clamp is not utilized and therefore, the skull clamp supporting structure, for example, a base unit, is also not used. The skull clamp and its supporting structure often provide attachment points and connectors for other devices, for example, an articulated arm and probe, a dynamic reference frame, a biopsy needle, etc. Thus, in order to provide a similar capability, the head support and stabilization device 310 has auxiliary brackets 312, 314. The respective structures of the auxiliary brackets 312, 314 are substantially identical; and therefore, only auxiliary bracket 312 will be described in detail.

The auxiliary bracket 312 has a generally horizontal arm 318 with one end fixed to a distal end 316 of a support shaft 22a. The arm 318 is connected to the support shaft 22a using, for example, adhesives, mechanical pins, etc. A distal end 322 of arm 318 has a pair of toothed or starburst connectors 324, 326 that have rings of teeth of different diameters. The different sizes of the connectors 324, 326 permit devices such as an articulated arm and probe, a dynamic reference frame, a biopsy needle, etc., to be attached to the head support and fixation system 310. It should be noted that toothed connectors can also be provided at other locations on the arm 318, either separately or as a concentric pair of connectors. The bracket 312 further includes a generally vertical post 328 having a lower end fixed to the distal end 322 of the arm 318. The post 328 has a cross-sectional profile that is noncircular, for example, generally hexagonal, and provides attachment locations for other devices, for example, a KANTWIST clamp, etc.

Figure 5:
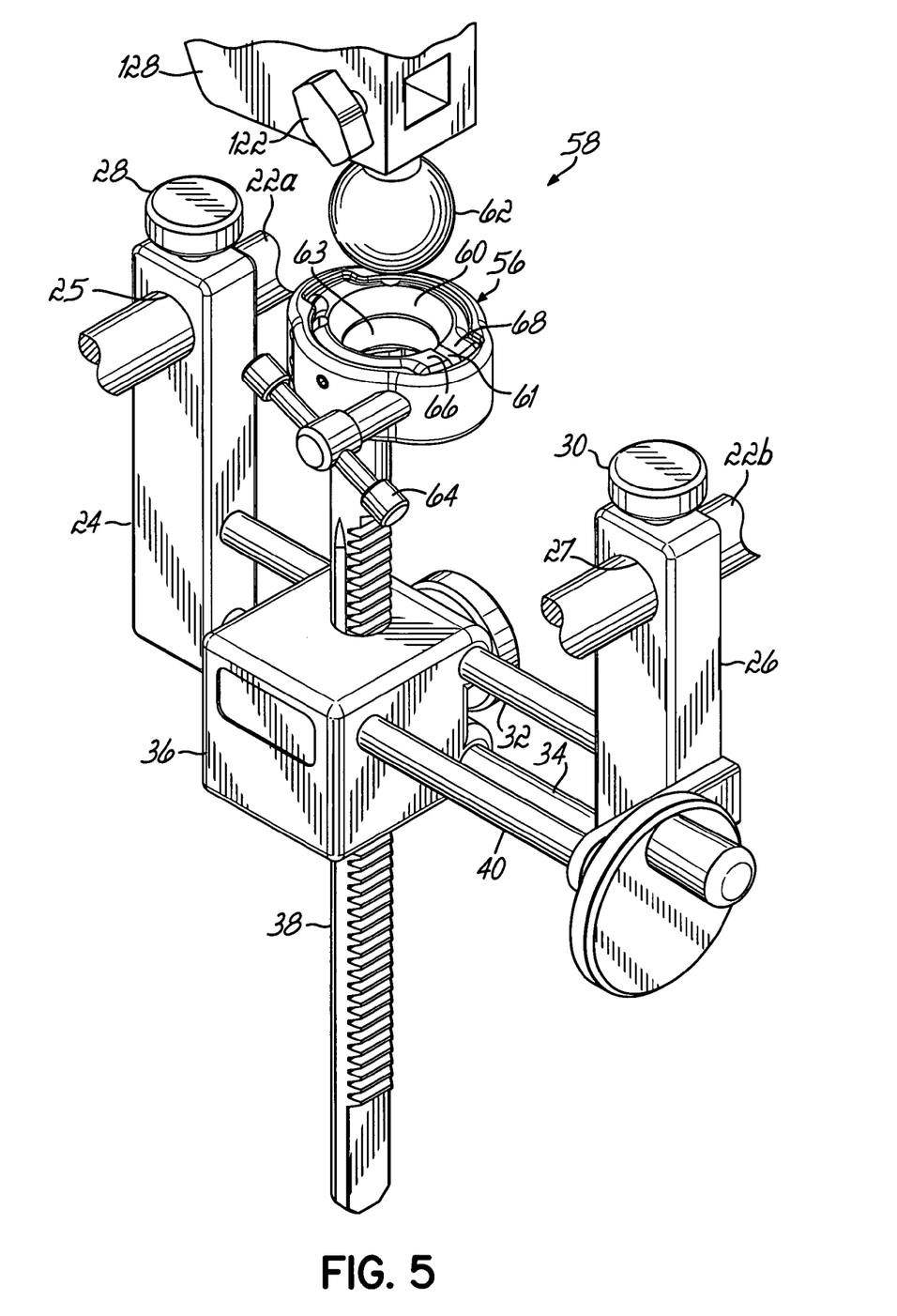
FIG. 5 is a perspective view of a disassembled view of a ball and socket support used with the head support and fixation system of FIG. 1.

The head support and stabilization device 310 is supported by a ball and socket joint 58 attached to an upper end of the rack 38. Referring to FIG. 5, a cage 56 is fixed to an upper end of the rack 38 and contains a socket 60 having a split 61. The socket 60 is pinned in the cage 56 and is sized slightly smaller than a ball 62. The split 61 spreads to permit the ball 62 to snap into an annular concave surface 63 of the socket 60, thereby forming the ball and socket joint 58. A locking screw 64 extends through the cage 56 and through a clearance hole in a first end 66 of the socket 60. The locking screw 64 is threaded into an opposite end 68 of the socket 60. With the locking screw 64 loosened, the ball 62 is freely pivotable with respect to the socket 60 and can be locked at any desired orientation therewith by tightening the locking screw 64.

Figure 1A:
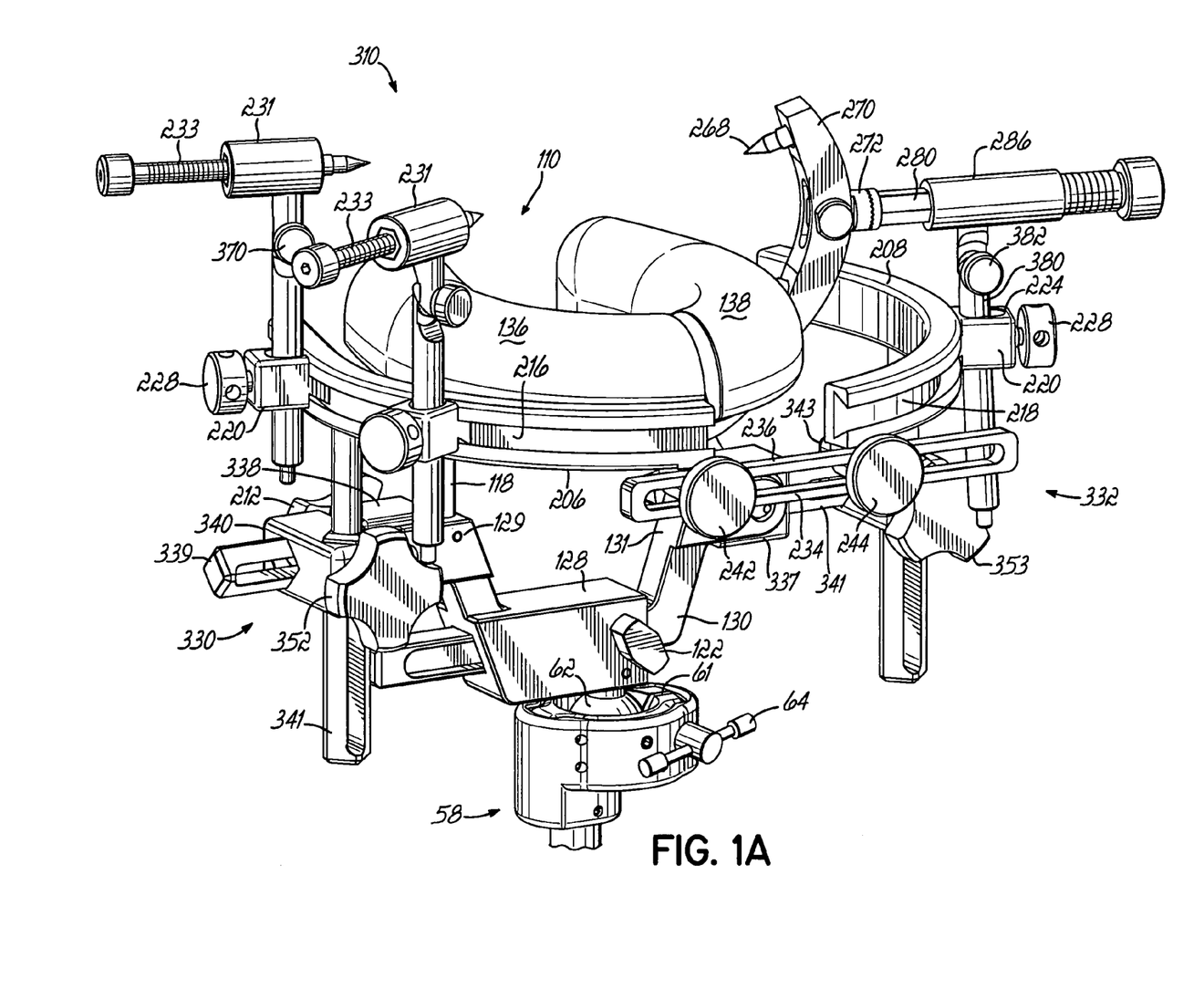
FIG. 1A is a second outer end perspective view of a head support and fixation system in accordance with the principles of the present invention.
Figure 2:
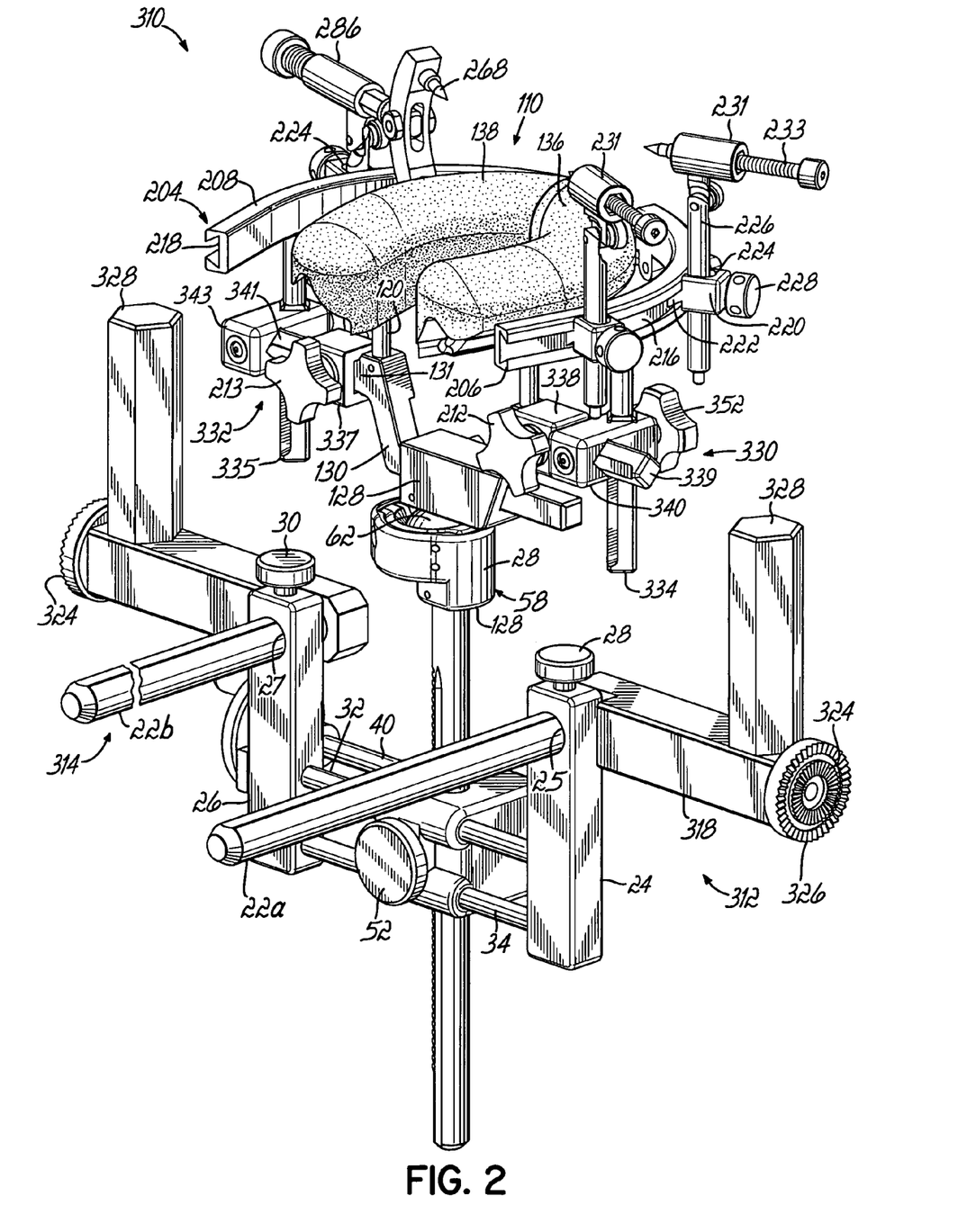
FIG. 2 is an inner perspective view of the head support and fixation system of FIG. 1.

Referring to FIG. 1A, the ball 62 is attached to a fixed bracket 128 that is pivotable with the ball in the ball and socket joint 58 and can be locked at any desired orientation by tightening the locking screw 64. A slide arm 130 is slidably mounted in the fixed bracket 128 and is movable laterally with respect to the fixed bracket 128. A locking screw 122 is threaded through the fixed bracket 128 and can be brought to bear against the slide arm 130, thereby securing the slide arm 130 at a desired location. The fixed bracket 128 has an outwardly extending mounting block 129; and a lower end of a mounting post of a horseshoe arm 118 is pinned to the mounting block 129. As shown in FIG. 2, the slide arm 130 has an outwardly extending mounting block 131; and a lower end of a mounting post of a horseshoe arm 120 is pinned to the mounting block 129. A head (not shown) is supportable by horseshoe pads 136, 138 that are mounted to respective horseshoe arms 118, 120 in a known manner. Thus, a fully adjustable horseshoe support 110 is provided by the pads, 136, 138, horseshoe arms 118, 120, fixed bracket 128, movable arm 130, ball and socket joint 58, rack 38, gear box 36, rods 32, 34 and support shafts 22.

Referring to FIG. 2, the mounting block 131 has a noncircular cross-sectional profile. An adaptor assembly 332 has a fixed member 337 that slides over the mounting block 131 and is secured in place by a locking screw 213 that extends through a wall of the fixed member 337 and is threaded into the mounting block 131. The fixed member 337 has a shaft 341 with a noncircular cross-sectional profile, and a movable member 343 is mounted on the shaft 341 and secured in place by a locking screw 353 (FIG. 1A). The mounting block 129 also has a noncircular cross-sectional profile. As shown in FIG. 2, an adaptor assembly 330 has a fixed member 338 that slides over the mounting block 129 and is secured in place by a locking screw 212 that extends through a wall of the fixed member 338 and is threaded into the mounting block 129. The fixed member 338 has a shaft 339 with a noncircular cross-section, for example, a square cross-sectional profile, and a movable member 340 is mounted on the shaft 339 and secured in place by a locking screw 352.

Figures 6, 7:
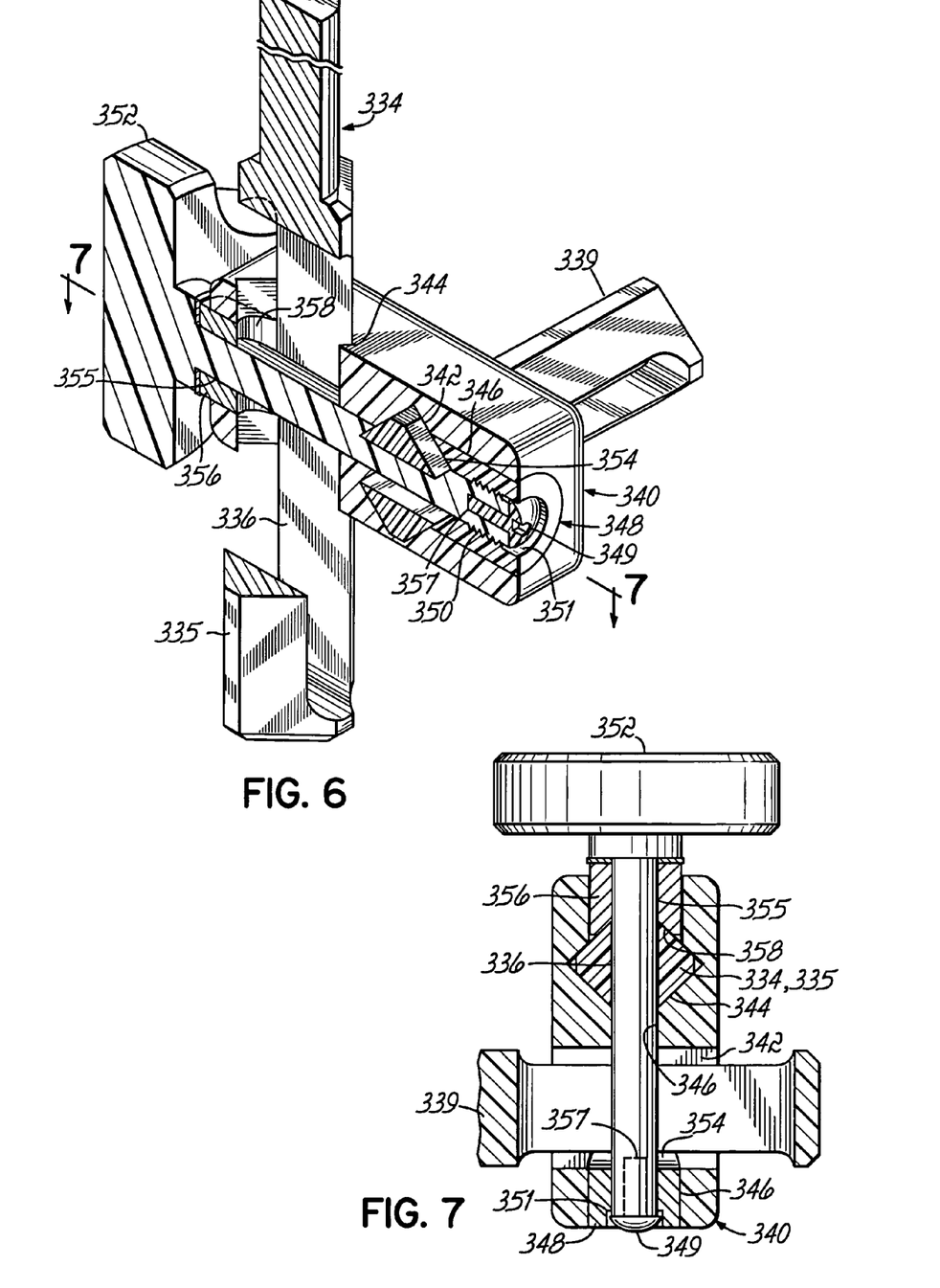
FIG. 6 is a centerline cross-sectional perspective view of an adapter used with the head support and fixation system of FIG. 1.
FIG. 7 is a cross-sectional view taken along line 7-7 of FIG. 6 of the adapter used with the head support and fixation system of FIG. 1.

The movable members 340, 343 are substantially identical in construction and therefore, only movable member 340 will be described in detail. Referring to FIGS. 6 and 7, a vertical support post 334 has a lower portion 335 with a noncircular cross-sectional profile, for example, a square cross-sectional profile, and a longitudinal, elongated slot 336. The movable member 340 has first, a generally horizontal through bore 342 with a cross-sectional profile that is substantially similar to, and slides over, the cross-sectional profile of the fixed member projecting shaft 339. The movable member 340 has a second, generally vertical through bore 344 that has a noncircular cross-sectional profile, for example, a square cross-sectional profile, that is sized to receive the cross-sectional profile of the lower portion 335 of the support post 334. The movable member 340 has a third, generally horizontal through bore 346 that is substantially mutually perpendicular to, and extends across, the through bores 342, 344. A cylindrical nut 348 is slidable into one end of the through bore 346 and has an internal threaded bore 350 that engages the threaded screw 352. The nut 348 has a notched end 354 that engages the noncircular cross-sectional profile of the projecting shaft 339, thereby preventing the nut 348 from rotating. The locking screw 352 passes through a clearance center bore 355 of a washer 356 that also extends into the movable member center bore 346. The washer 356 also has a notched end 358 that conforms around the noncircular cross-sectional profile of the lower portion 335 of the support shaft 334 and prevents the washer 356 from rotating.

The cylindrical nut 348 has a counterbore 351 on an outer end that is sized to receive a head of a cap screw 349. The cap screw 349 is threaded into a centerbore 357 in a distal end of the locking screw 352, and thus, the cap screw 349 prevents the locking screw 352 from being removed from the movable member 340. A low friction washer (not shown) may be optionally used below the head of the cap screw 349.

As shown in FIG. 2, the support posts 334, 335 support respective fixation arcs 206, 208 of a fixation arc assembly 204. Upon loosening the locking screw 352, the fixation arc 206 is movable vertically with respect to the movable member 340 as well as laterally along the projecting shaft 339 of the fixed member 338, thereby providing a wide range of adjustability of the fixation arc 206 with respect to the pad 136 and a patient's head. When the desired position of the fixation arc 206 is achieved, the locking screw 252 is tightened, thereby bringing the nut 348 (FIG. 6) in tight engagement with the projecting shaft 339 of the fixed member 338 and locking the movable member 340 with respect to the fixed member 338. In addition, the washer 356 is brought into tight engagement with the support post 334, thereby securing the support post 334 in its desired vertical position. The fixation arc 208 may be adjusted vertically and laterally in a similar manner using the locking screw 353 of FIG. 1A.

As shown in FIG. 2, each of the fixation arcs 206, 208 has respective dovetail slots 216, 218. Skull pins 233 are supported by respective pin post carriers and can be mounted at different locations in the fixation arcs 206, 208. The pin post carrier 220 has a dovetail 222 that slides in the dovetail slots 216, 218, and the pin post carrier 220 has an elongated hole 224 that extends into the dovetail 222. A pin post 226 is insertable into the elongated hole 224. A locking screw 228 is threaded into the pin post carrier 220 and has an end that extends into the hole 224 and bears against the pin post 226. As the locking screw 228 is tightened, the pin post 226 is pushed across the elongated hole 224 until it is close to an outer edge 232 of the fixation arc 206. The pin post carrier 220 can be moved circumferentially in the dovetail slot 216 to a desired location, and the pin post 226 can be adjusted vertically to a desired position. Further tightening of the locking screw 228 clamps the pin post 226 against the fixation arc outer surface 232, thereby securing the pin post 226 at a desired elevation with respect to the pin post carrier 220 and further securing the pin post carrier 220 at a desired location in the dovetail slot 216. A pin screw guide 231 has internal threads for receiving the threaded skull pin 233. Thus, any number of skull pins 233 can be located on either one of the fixation arcs 206, 208 at locations with respect to a patient's head. The skull pins 233 help to provide a desired lateral stabilization, that is, fixation or stabilization of a patient's head in a generally horizontal direction.

Referring to FIG. 1A, outer ends of the fixation arcs 206, 208 are rigidly connected together by a stabilizer bar 234. The stabilizer bar 234 has a longitudinal slot 236 that receives threaded shafts of respective locking screws 242, 244. The locking screws 242, 244 are threaded into respective integral bosses extending downward from the outer ends of the respective fixation arcs 206, 208, thereby clamping and stabilizing the outer ends of the fixation arcs 206, 208. The stabilizing bar 234 substantially improves the rigidity of the fixation arc assembly 204.

Figure 8:
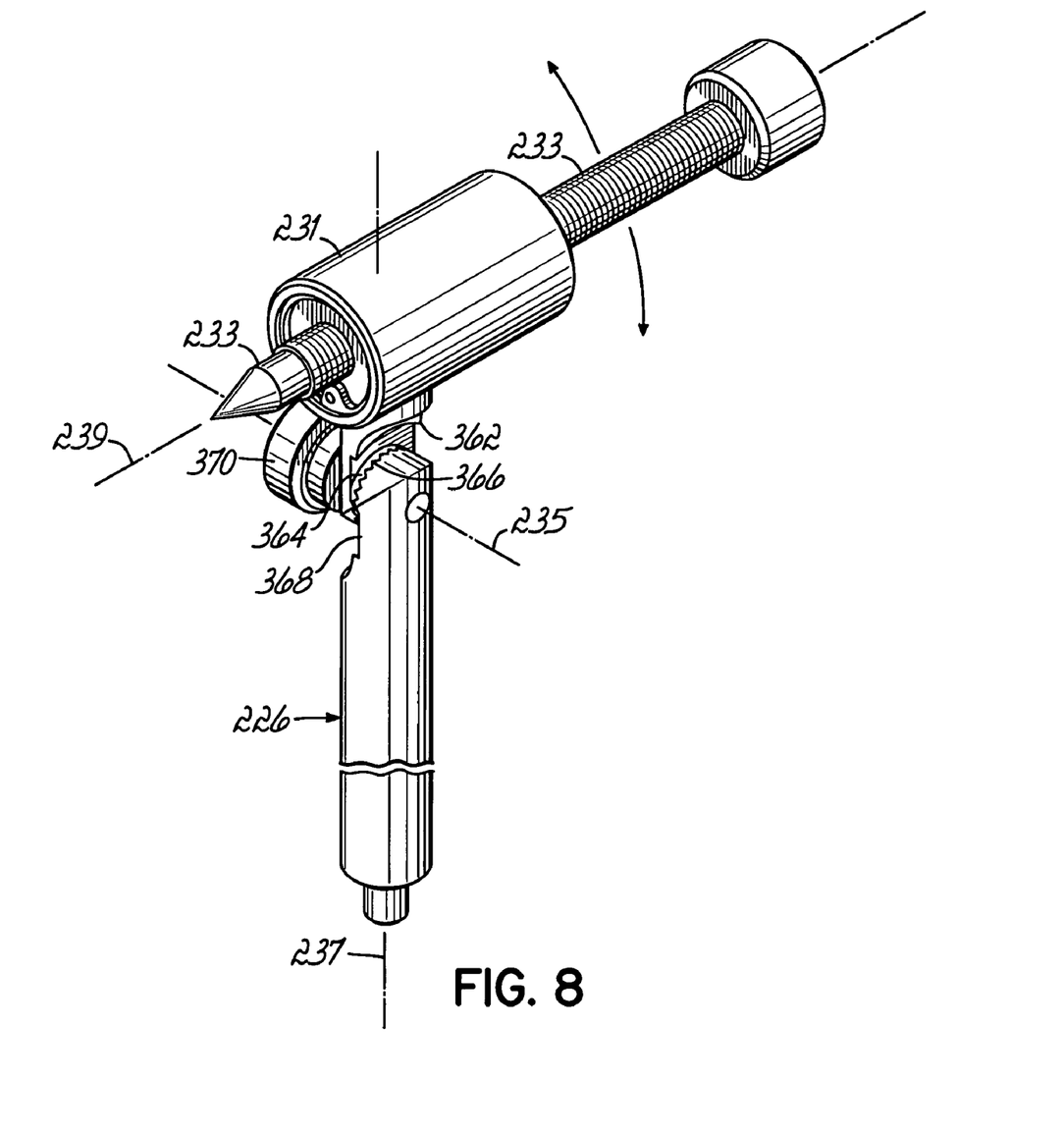
FIG. 8 is a perspective view of a tiltable skull pin used with the head support and fixation system of FIG. 1.

Referring to FIG. 8, the head support and fixation system of the present invention provides a skull pin 233 that is tiltable with respect to a generally horizontal axis of rotation 235. The pin screw guide has a generally downward extending support arm 362. A lower end of the support arm has a starburst connector 364 having a ring of teeth that is engageable with an opposing starburst connector 366 having a mating ring of teeth. The opposing connector 366 is disposed on an upper end 368 of a pin post 226. A locking screw 370 extends through a clearance hole in the support arm connector 362 and into a threaded hole in the upper end 368 of the pin post 226. Thus, by loosening the locking screw 370, the skull pin 233 and pin screw guide 360 can be tilted with respect to a generally horizontal axis of rotation 235. When the skull pin 233 has been tilted to a desired angle, the locking screw 370 is tightened, thereby engaging the opposing toothed connectors 364, 366 and securing the skull pin at its desired angular orientation. Thus, the pin 233 has a length or centerline 239 that is rotatable with respect to a first axis of motion 235 that is substantially perpendicular to the pin centerline 239. Further, the pin 233 and pin post 226 are rotatable within a pin post carrier 220 (FIG. 2); and therefore, the pin centerline 239 is rotatable with respect to a second axis of motion 237 that is also substantially perpendicular to the pin length or centerline 239.

Figure 9A:
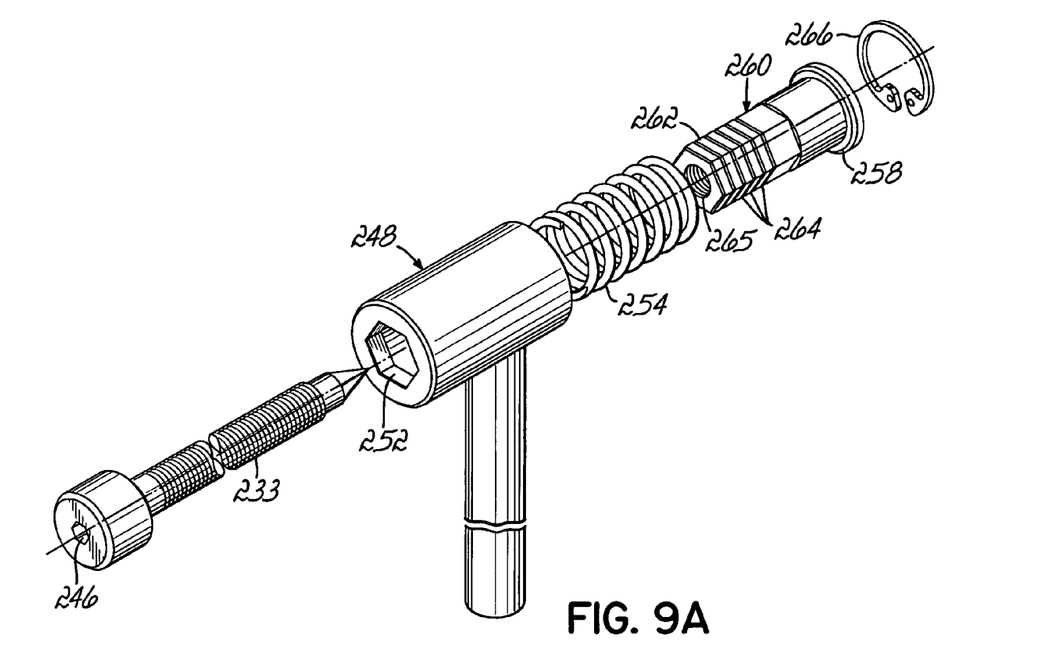
FIG. 9A is a disassembled perspective view of a skull pin with a load indicator that can be used with the head support and fixation system of FIG. 1.
Figure 9B:
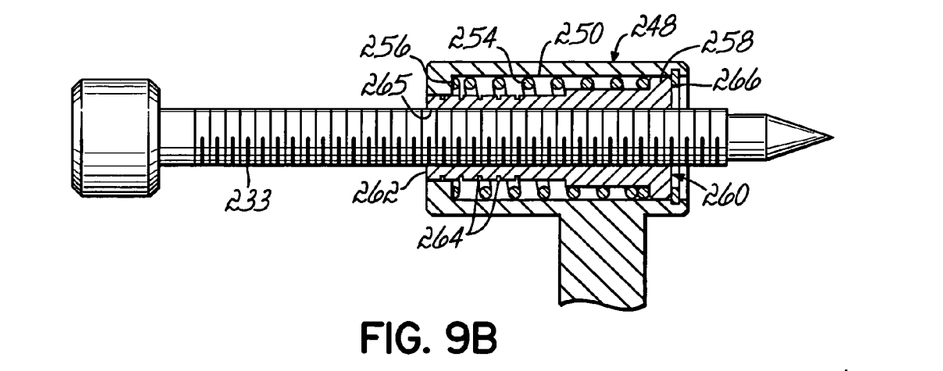
FIG. 9B is a centerline cross-sectional view of a skull pin with a load indicator that can be used with the head support and fixation system of FIG. 1 and illustrating the skull pin in an unloaded state.
Figure 9C:
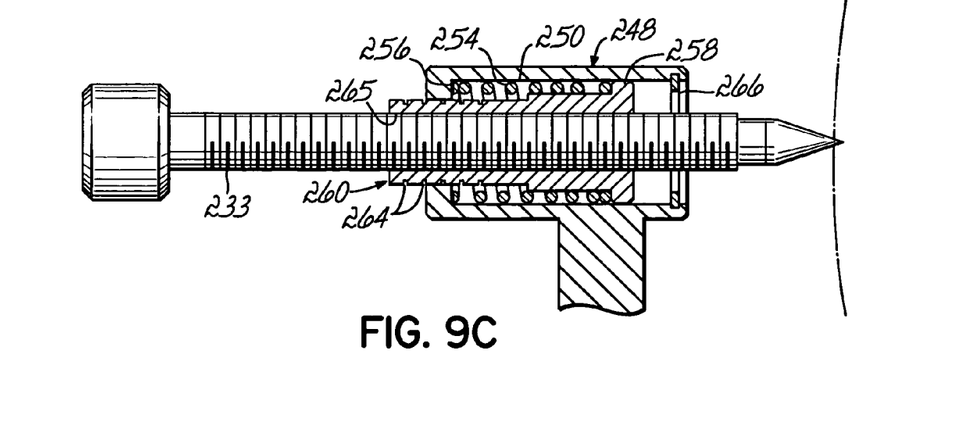
FIG. 9C is a centerline cross-sectional view of a skull pin with a load indicator that can be used with the head support and fixation system of FIG. 1 and illustrating the skull pin in a loaded state.

It is often desirable to tighten the skull pins with a known load. As shown in FIGS. 9A and 9B, an outer end of each of the threaded skull pins 233 has a hexagonal shaped opening 246 that is sized to receive a torque wrench. Thus, the skull pins 233 can be tightened to any desired force and used with a pin screw guide 248 that provides a load indicator. The pin screw guide 248 has an internal bore 250 that terminates with a hexagonal broached hole 252. A compression spring 254 is inserted into the bore 250 and is captured between one end 256 of the pin screw guide 248 and an end flange 258 of an insert 260 also located in the bore 250 and inside the compression spring 254. The insert 260 has one end 262 with a hexagonal cross-sectional profile that slides through the hexagonal opening 252. The insert 260 is secured in the bore 250 by a snap ring 266. The hexagonal end 262 has graduations 264 indicating a force being applied by the skull pin 233 against the head. The graduations 264 may be calibrated to represent any increment of force, for example, 10 pounds. The skull pin 233 is threaded into an internal bore 265 of the insert 260 and contacts the head. As shown in FIG. 9C, as the skull pin 233 is tightened, the reactive force of a head against the skull pin 233 causes the insert 260 to extend out of the opening 252 a distance proportional to the force being applied by the pin 233.

Figure 10A:
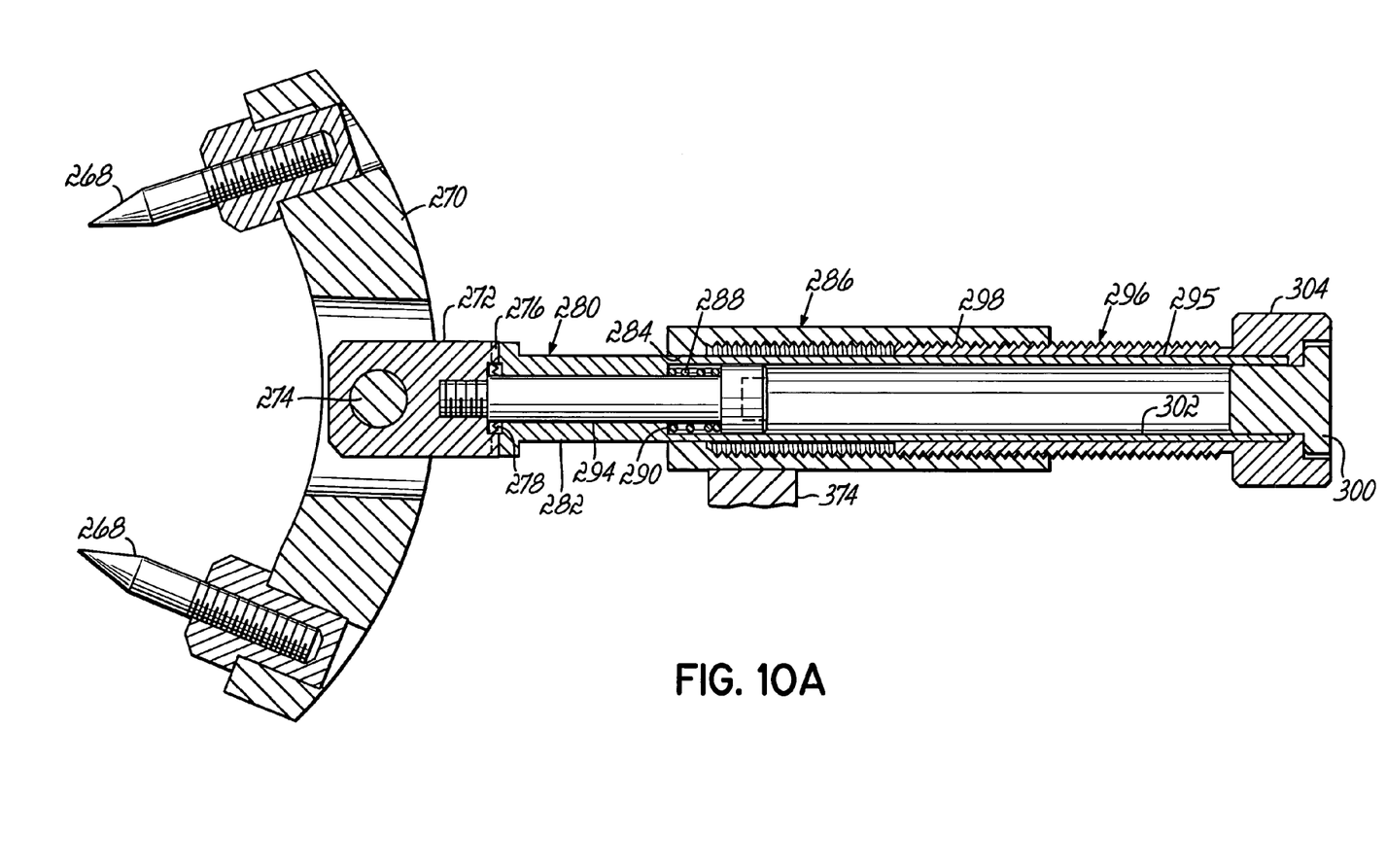
FIG. 10A is a centerline cross-sectional view of a tiltable rocker arm supporting fixed skull pins that can be used with the head support and fixation system of FIG. 1.
Figure 10B:
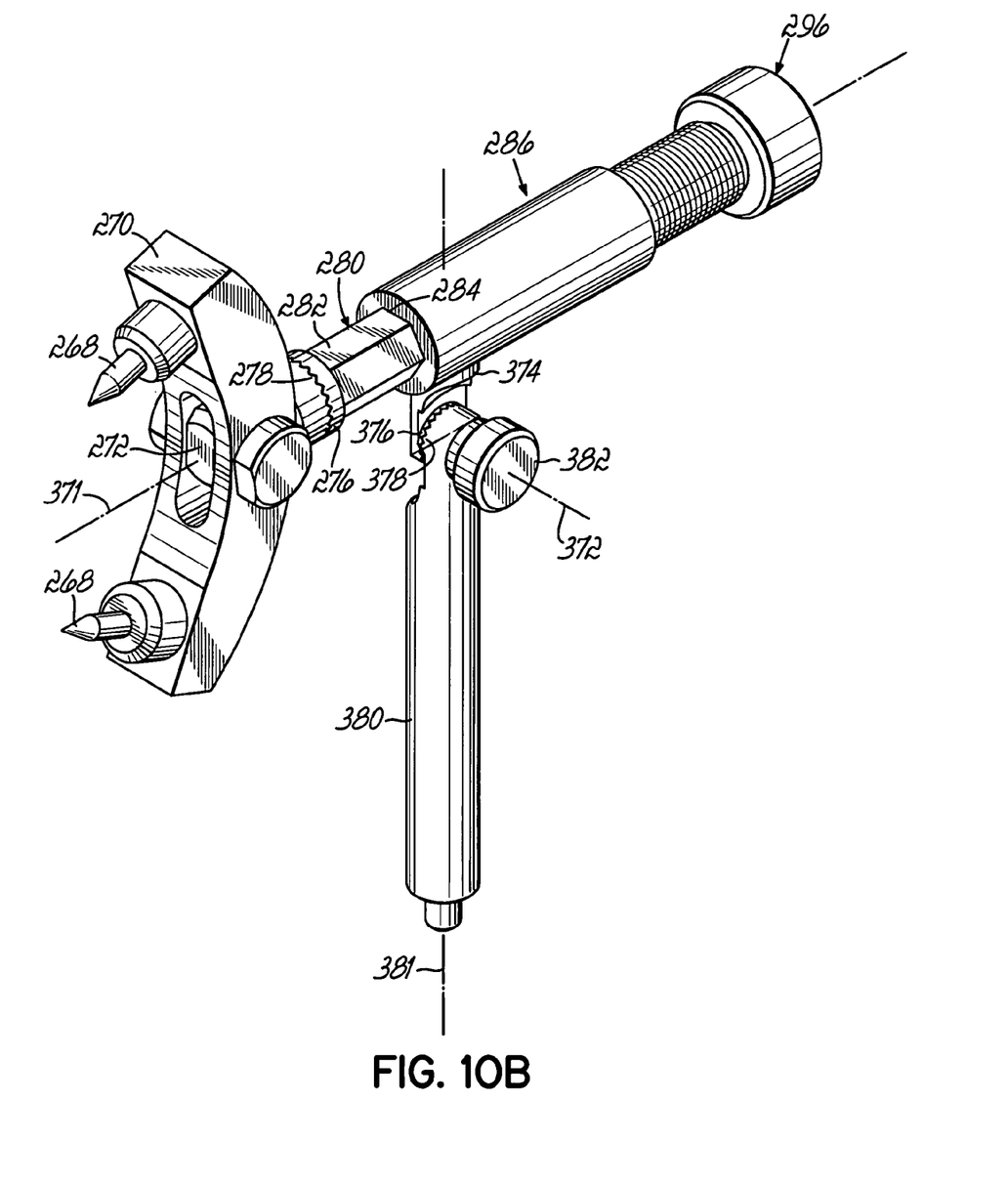
FIG. 10B is a perspective view of the tiltable rocker arm supporting fixed skull pins of FIG. 10A.

Referring to FIGS. 10A and 10B, in some procedures, it is desirable to provide skull pins 268 in a rocker arm 270 that is pivotally connected to a clevis 272 via a pivot pin 274. The clevis 272 has a ring of teeth 276 that engages with a mating ring of teeth 278 on the end of a piston 280. One end 282 of the piston has a hexagonal cross-sectional profile that mates with, and slides inside of, a broached hexagonal hole 284 in an end of a screw guide 286. A compression spring 288 is captured between an inner wall 290 of the piston 280 and a head of a cap screw 292. The cap screw 292 extends through a piston center bore 294 and is threaded into the clevis 272. Therefore, if it is desired to change the angular orientation of the rocker arm 270 and clevis 272 with respect to the piston 280, the rocker arm 270 is pulled away from the piston 280, that is, to the left as viewed in FIGS. 10A and 10B, thereby disengaging the opposed rings of teeth 276, 278. The rocker arm 270 may then be rotated to any desired orientation and released. The compression spring 288 pulls the clevis 272 back into contact with the end of the piston 280, and the engagement of the opposed rings of teeth 276, 278 secures the clevis 272 and rocker arm 270 in the desired orientation on the piston 280.

An opposite end 295 of the piston 280 has a circular cross-sectional profile and is mounted for rotation in a center bore of an adjusting screw 296 that, in turn, is threaded into a bore 298 of the screw guide 286. A retaining cap 300 extends through an end of the adjusting screw 296 and is press fit into a center bore 302 of the piston 280. Thus, the retaining cap 300 is effective to secure the piston 280 longitudinally with respect to the adjusting screw 296. Rotation of an adjustment knob 304 causes the adjusting screw 296, piston 280 and clevis 272 to move axially. The adjusting screw 296 rotates about the nonrotatable cap 300 and piston 280, and the hexagonally-shaped piston end 282 slides axially through the hexagonally-shaped hole 284 in the end of the screw guide 286, thereby adjusting the axial position of the skull pins 268 with respect to a patient's head.

Referring to FIG. 10B, the pins 268, rocker arm 270, piston shaft 280 and screw guide 286 are tiltable with respect to a generally horizontal axis of rotation 372. The screw guide 286 has a generally downward extending support arm 374. A lower end of the support arm 374 has a starburst connector 376 having a ring of teeth that is engageable with an opposing starburst connector 378 having a mating ring of teeth. The opposing connector 378 is disposed on an upper end of a pin post 380. A locking screw 382 extends through a clearance hole in the upper end of the pin post 380 and is threaded into a hole in the lower end of the support arm 374. Thus, by loosening the locking screw 382, the pins 268, rocker arm 270, piston shaft 280 and screw guide 286 can be tilted with respect to a generally horizontal axis of rotation 372. When a desired angle is achieved, the locking screw 382 is tightened, thereby engaging the opposing toothed connectors 376, 378 and securing the pins 268 and rocker arm 270 at a desired angular orientation with respect to a patient's head. Thus, the rocker arm 270 and clevis 272 are rotatable about a centerline 371 that is rotatable with respect to a first axis of motion 372 that is substantially perpendicular to the centerline 371. Further, the rocker arm 270 and clevis 272 and supporting pin post 380 are rotatable within a pin post carrier 220 (FIG. 1A); and therefore, the centerline 371 is rotatable with respect to a second axis of motion 381 that is also substantially perpendicular to the centerline 371.

In use, referring to FIG. 1, prior to surgery, the pads 136, 138 are adjusted for elevation using the crank rod 40 and are adjusted for lateral spacing using the locking screw 122 and movable arm 130. The orientation of the pads 136, 138 can be adjusted using the locking screw 64 and the ball and socket joint 58. Those adjustments are first made so that the head support 110 provides a desired subjacent support for the static load of a patient's head. Thereafter, the screws 242, 244 are loosened, and locking screws 252, 253 are used to place the fixation arcs 206, 208 at an initial elevation and lateral position relative to the patient's head. Thereafter, pin post carriers 220 are mounted in dovetail slots 216, 218 of respective fixation arcs 206, 208 in order to place skull pins 233 on one side of the patient's head and skull pins or a rocker arm 270 on an opposite side. The skull pins 233 and rocker arm 270 can be tilted using respective locking screws 370 and 382. When in the fixation arcs 206, 208 are in their desired positions, the locking screws 242, 244 are tightened to provide rigidity to the fixation arcs 206, 208. Final positioning adjustments are made, and the skull pins are tightened to bring them to their desired clamping force using the load indicators 264 of FIG. 100, thereby providing a desired lateral stabilization of the patient's head. In the process of supporting and stabilizing the patient's head, surgical draping is applied to the patient and portions of the head support system 310 in a known manner. Depending on the surgery being performed, it may be required to lower the horseshoe support 110 out of contact with the patient's head and subsequently, raise the horseshoe support 110 back into contact with the patient's head. With the present invention, the length of the crankrod 40 places the crankrod end at an outer, lateral position, so that it is more accessible and can be reached with minimal disturbance of the surgical draping. Further, the crankrod 40 can be rotated with one hand to lower or raise the head support pads 136, 138 and its worm gear construction mechanically locks the head support at a desired elevation without requiring a separate locking pin or screw.

The head support and stabilization system 310 has an advantage of providing independent and flexible support structures to provide both a static head support and head stabilization for stabilizing a skull during neuro-navigational and surgical procedures. The head support system permits a head support to be adjusted and simultaneously locked at any elevation with a common motion of only one hand. Such a combination of static load support and stabilization is especially useful when working with pediatric patients and in plastic surgery. Further, the components of the head support systems are easily disassembled for ease of cleaning.

While the present invention has been illustrated by a description of an embodiment, and while such embodiment has been described in considerable detail, there is no intention to restrict, or in any way limit, the scope of the appended claims to such detail. Additional advantages and modifications will readily appear to those skilled in the art. For example, in the described embodiment, various locking screws are shown passing through two or more members in one direction and engaging a threaded bore. As will be appreciated, in other embodiments, the orientation of the locking screws can be reversed, so that it passes through the components in an opposite direction.

In the described embodiment, the vertical posts 24, 26 are shown extending below the respective support shafts 22a, 22b. As will be appreciated, in an alternative embodiment where connections for the support shafts 22a, 22b to a table are lower or it is desired to have more height, the vertical posts 24, 26 can be inverted. The guide rods 32, 34 and gear box 36 are first removed from the posts 24, 26; and the posts 24, 26 are inverted on the support shafts 22a, 22b. The gear rack 38 is removed from the gear box 36; and the guide rods and gear box are mounted on the posts 24, 26. The gear rack 38 is then inserted in an opposite side of the gear box 36.

Therefore, the invention in its broadest aspects is not limited to the specific details shown and described. Consequently, departures may be made from the details described herein without departing from the spirit and scope of the claims which follow.

What is claimed is:

1. A system for supporting a patient's head comprising:
   an arcuate member adapted to be positioned adjacent to and to provide support for the head, the arcuate member including a corresponding outwardly directed arcuate slot;
   a carrier adapted to be received within, movable along, and secured with respect to the slot;
   a pin post held by the carrier;
   a pin supported by the pin post via a lockable connector; and
   the lockable connector further comprising a first member supporting the pin and a second member disposed on the pin post, the first member being rotatable with respect to the pin post, the lockable connector being operable to secure the first member and pin at a desired angle with respect to the second member and pin post, wherein the first member and the second member are toothed connectors.

2. The head support system of claim 1 wherein the lockable connector further comprises a locking screw extendable through a clearance bore in one of the first member and the second member and engaging a threaded bore in another of the first member and the second member.

3. The head support system of claim 2 further comprising a pin guide having a threaded bore receiving the pin and the first member is disposed on the pin guide.

4. The head support system of claim 3 wherein the pin guide further comprises a support arm comprising one end connected to the pin guide and an opposite end supporting the first member of the lockable connector.

5. The head support system of claim 4 wherein the second member of the lockable connector is disposed at an upper end of the pin post.

6. The head support system of claim 1 further comprising:
   at least one additional carrier, additional pin post, additional pin, and additional lockable connector, whereby each of the pins is adapted to engage the patient's head generally above the location of a corresponding carrier secured to the arcuate member.

7. The system of claim 6 and further comprising:
   a third carrier adapted to be received within, movable along, and lockable to the slot;
   a third pin post held by the third carrier;
   a rocker arm holder located above the third pin post;
   a third lockable connector connecting the rocker arm holder to the third pin post, the third lockable connector including an upper member supporting the rocker arm holder and a lower member disposed on the third pin post, the upper member being rotatable with respect to the lower member, the third lockable connector being operable to secure the upper member and the rocker arm holder at a desired angle with respect to the lower member and the third pin post;
   a rocker arm held by the rocker arm holder so as to rotatable about a rocker arm axis; and
   a pair of pins held in spaced relation by the rocker arm, whereby the rocker arm's rotatability about the rocker arm axis enables the pair of pins to be located at a desired orientation relative to the rocker arm axis.

\* \* \* \* \*